United States Patent
Karrer et al.

[11] Patent Number: 5,952,262
[45] Date of Patent: *Sep. 14, 1999

[54] PREPARATION OF AROMATIC OR HETEROAROMATIC NITRILES

[75] Inventors: Lothar Karrer, Pfungstadt; Frank-Friedrich Pape, Kleinniedesheim; Heinz-Josef Kneuper, Mannheim; Michael Hüllmann, Bensheim, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/723,915

[22] Filed: Sep. 30, 1996

[30] Foreign Application Priority Data

Oct. 7, 1995 [DE] Germany .............. 195 37 446

[51] Int. Cl.⁶ .............. B01J 23/16; C07C 253/12
[52] U.S. Cl. .............. 502/353; 558/319; 558/327; 558/328
[58] Field of Search ............... 558/329, 328, 558/319, 327

[56] References Cited

U.S. PATENT DOCUMENTS

| | | | |
|---|---|---|---|
| 3,462,476 | 8/1969 | O'Donnell et al. | 260/465 |
| 3,870,743 | 3/1975 | Ibing et al. | 260/465 |
| 4,107,085 | 8/1978 | Sasaki et al. | 252/448 |
| 4,178,304 | 12/1979 | Litvishkov et al. | 260/465 |
| 4,410,450 | 10/1983 | Sasaki et al. | 502/22 |
| 4,590,173 | 5/1986 | Sasaki et al. | 502/204 |
| 4,784,979 | 11/1988 | Toft et al. | 502/8 |
| 4,814,479 | 3/1989 | Engelbach et al. | 558/328 |

FOREIGN PATENT DOCUMENTS

57/130546 8/1982 Japan .

*Primary Examiner*—Johann Richter
*Assistant Examiner*—Ebenezer Sackey
*Attorney, Agent, or Firm*—John H. Shurtleff

[57] ABSTRACT

Preparation of aromatic or heteroaromatic nitrites of the formula I

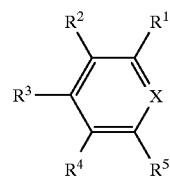

where X is nitrogen or C-R⁶ and all of the R substituents represent hydrogen, alkyl, halogen, nitro, amino or similar groups, provided at least one substituent is a cyano or alkylcyano group. The nitrites I are produced by reacting aromatic or heteroaromatic hydrocarbons of the formula II

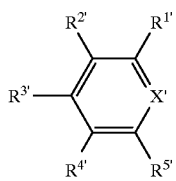

where X is nitrogen or C-R⁶, provided at least one substituent is $C_1$–$C_8$-alkyl, with ammonia and oxygen at 200 to 600° C. under a pressure of 0.1 to 5 bar in the gas phase over a supported catalyst containing 0.5 to 20% by weight of vanadium oxide. The supported catalyst consists of from 2 to 30 particle fractions whose mean diameters differ by from 10 to 80% and the supporting carrier of the catalyst has a bulk density of 0.6 to 1.2 kg/liter.

11 Claims, No Drawings

PREPARATION OF AROMATIC OR HETEROAROMATIC NITRILES

The present invention relates to a process for the preparation of aromatic or heteroaromatic nitriles from aromatic or heteroaromatic hydrocarbons with ammonia and oxygen or oxygen-containing gases at elevated temperatures in the gas phase over novel supported catalysts which contain vanadium oxide and consist of from two to thirty particle fractions whose mean diameters differ by from 10 to 80% and in which the carrier has a certain bulk density.

EP-A-222 249 discloses a process for the preparation of aromatic nitriles from alkyl-substituted aromatic hydrocarbons by catalytic oxidation with ammonia and oxygen or oxygen-containing gases at elevated temperatures in the vapor phase in the presence of a catalyst which contains from 2 to 10% by weight of vanadium pentoxide, from 1 to 10% by weight of antimony trioxide, from 0.02 to 2% by weight of an alkali metal oxide and from 0.01 to 1% by weight of an alkaline earth metal oxide on alumina. These catalysts consist of only one particle fraction.

DE-A-28 10 856 discloses a process for the preparation of o-aminobenzonitrile from o-toluidine by catalytic oxidation with ammonia and oxygen at elevated temperatures in the vapor phase in the presence of a catalyst which contains from 1 to 9% by weight of vanadium oxide, from 5 to 12% by weight of antimony oxide, from 3 to 9% by weight of bismuth oxide and from 0.5 to 4% by weight of phosphorus oxide on a carrier. These catalysts, too, consist only of one particle fraction.

In the processes known to date, the oxygen uptake of the catalyst and the yields were unsatisfactory.

It is an object of the present invention to remedy the abovementioned disadvantages.

We have found that this object is achieved by a novel and improved process for the preparation of aromatic or heteroaromatic nitriles of the general formula I

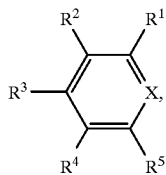

(I)

where

X is nitrogen or C-$R^6$ and $R^1$, $R^2$, $R^3$, $R^4$, $R^5$ and $R^6$ are each hydrogen, $C_1$–$C_8$-alkyl, halogen, trifluoromethyl, nitro, amino, cyano, $C_1$–$C_7$-cyanoalkyl, $C_1$–$C_8$-aminoalkyl or hydroxyl, with the proviso that at least one of the substituents is cyano or $C_1$–$C_7$-cyanoalkyl, from aromatic or heteroaromatic hydrocarbons of the general formula II

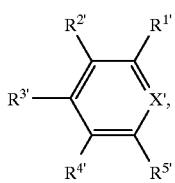

(II)

where

X' is nitrogen or C-$R^{6'}$ and $R^{1'}$, $R^{2'}$, $R^{3'}$, $R^{4'}$, $R^{5'}$ and $R^{6'}$ are each hydrogen, $C_1$–$C_8$-alkyl, halogen, trifluoromethyl, nitro, amino, $C_1$–$C_8$-aminoalkyl or hydroxyl, with the proviso that at least one of the substituents is $C_1$–$C_8$-alkyl, with ammonia and oxygen or oxygen-containing gases at from 200 to 600° C. and from 0.1 to 5 bar in the gas phase over supported catalysts which contain from 0.5 to 20% by weight of vanadium oxide, wherein the supported catalysts consist of from 2 to 30 particle fractions whose mean diameters differ by from 10 to 80% and the carrier has a bulk density of from 0.6 to 1.2 kg/l, and novel supported catalysts.

The novel process can be carried out as follows:

A mixture of an aromatic or heteroaromatic hydrocarbon, ammonia and oxygen or an oxygen-containing gas can be reacted in the gas phase at from 200 to 600° C., preferably from 300 to 550° C., particularly preferably from 350 to 500° C., and from 0.1 to 5, preferably from 0.3 to 2, particularly preferably from 0.5 to 1.5, bar, in particular at atmospheric pressure, in the presence of a supported catalyst which consists of from 2 to 30, preferably from 2 to 10, particularly preferably from 2 to 5, ie. 2, 3, 4 or 5, in particular 2 or 3, particle fractions whose mean diameters differ by from 10 to 80%, preferably from 10 to 70%, particularly preferably from 30 to 60%, and in which the carrier has a bulk density of from 0.6 to 1.2, preferably from 0.6 to 1.0, particularly preferably from 0.6 to 0.9, kg/l, in a fixed bed or, preferably, in a fluidized bed.

The starting compounds are preferably taken up in a gas stream of ammonia and an oxygen-containing gas, such as air, their concentration advantageously being brought to 0.1–25, preferably 0.1–10, % by volume.

Suitable supported catalysts are those having carriers comprising alumina, silica, titanium dioxide, zirconium dioxide, silicon carbide, magnesium oxide or mixtures thereof, preferably alumina, silica, titanium dioxide, zirconium dioxide or mixtures thereof, particularly preferably alumina, silica or mixtures thereof, and from 0.5 to 20, preferably from 1 to 10, particularly preferably from 3 to 8, % by weight of vanadium oxide and from 0 to 20, preferably from 0.5 to 20, particularly preferably from 1 to 10, in particular from 2 to 8, % by weight of antimony oxide and from 0 to 4, preferably from 0.01 to 4, particularly preferably from 0.05 to 3, % by weight of cesium oxide, rubidium oxide or mixtures thereof and from 0 to 10, preferably from 0 to 5, particularly preferably from 0 to 3, % by weight of one or more oxides selected from the group consisting of oxides of tungsten, of molybdenum, of titanium, of iron, of cobalt, of nickel, of manganese and of copper, or an alkali metal or alkaline earth metal, the carrier accounting for from 50 to 99.9% by weight of the total catalyst mass.

The supported catalysts can be prepared by simultaneous or successive impregnation of the carrier with any desired solutions, preferably with an aqueous solution or a suspension of one or more compounds of the active catalyst components, such as vanadium and, if required, antimony, cesium, rubidium, tungsten, molybdenum, titanium, iron, cobalt, nickel, manganese, copper, alkali metal, alkaline earth metal, drying and calcination under oxidizing conditions at from 400 to 800° C., preferably from 450 to 750° C. Preferably, the impregnating solution or suspension is used in an amount which is not greater than that which can be taken up by the carrier. The impregnation can also be carried out in a plurality of steps after intermediate drying in each case.

The impregnating solutions used are as a rule the active components preferably in the form of aqueous solutions or their salts, in particular of salts of organic acids which can be decomposed in the oxidative calcination without leaving residues. The oxalates, particularly in the case of vanadium, and the tartrate, particularly in the case of antimony and of tungsten, are preferred here, and the tartrates may also be present in the form of mixed salts, for example with ammonium ions. For the preparation of such solutions, the metal oxides may be dissolved in the acids.

The carriers having different mean particle sizes can be combined before or, preferably, after the impregnation processes and preferably thoroughly mixed.

The substituents $R^1$, $R^2$, $R^3$, $R^4$, $R^5$, $R^6$, $R^{1'}$, $R^{2'}$, $R^{3'}$, $R^{4'}$, $R^{5'}$ and $R^{6'}$ and the links X and X' have the following meanings:

X and X' are each
  nitrogen or C-$R^6$, preferably C-$R^6$,
$R^1$, $R^2$, $R^3$, $R^4$, $R^5$, $R^6$, $R^{1'}$, $R^{2'}$, $R^{3'}$, $R^{4'}$, $R^{5'}$ and $R^{6'}$ are each
  hydrogen,
  $C_1$–$C_8$-alkyl, preferably $C_1$–$C_4$-alkyl, particularly preferably methyl, ethyl, n-propyl or isopropyl,
  halogen such as fluorine, chlorine, bromine or iodine, preferably fluorine, chlorine or bromine, particularly preferably chlorine or bromine, in particular chlorine,
  trifluoromethyl,
  nitro,
  amino,
  $C_1$–$C_8$-aminoalkyl, preferably $C_1$–$C_4$-aminoalkyl, particularly preferably aminomethyl, 1-aminoethyl or 2-aminoethyl,
  hydroxyl,
$R^1$, $R^2$, $R^3$, $R^4$, $R^5$ and $R^6$ are additionally each
  cyano,
  $C_1$–$C_7$-cyanoalkyl, preferably $C_1$–$C_3$-cyanoalkyl, particularly preferably cyanomethyl, 1-cyanoethyl or 2-cyanoethyl,
with the proviso that at least one, ie. 1, 2, 3, 4, 5 or 6, preferably 1, 2 or 3, particularly preferably 1 or 2, in particular one, of the substituents is or are cyano or $C_1$–$C_7$-cyanoalkyl.

The ammoxidation is of particular industrial importance for the preparation of phthalodinitrile from o-xylene, of isophthalodinitrile from m-xylene, of terephthalodinitrile from p-xylene, of benzonitrile from toluene and of nicotinonitrile from β-picoline.

In the case of the xylenes, the ammoxidation of the first methyl group takes place more rapidly than that of the second one, so that partial ammoxidation products, eg. p-methylbenzonitrile from p-xylene, o-methylbenzonitrile from o-xylene and possibly benzonitrile as a by-product, can also be readily obtained.

EXAMPLE

Catalyst A 1000 g of spherical alumina (Puralox® SCC a 150/120 from Condea-Chemie) which had a bulk density of 0.8 kg/l was impregnated in a mixer with 930.4 g of an aqueous solution which had been prepared from 351.4 g of distilled water, 150 g of 25% strength ammonia solution, 65.5 g of antimony(III) oxide, 56.2 g of vanadic acid (90% by weight of vanadium(V) oxide), 6 g of potassium nitrate, 150 g of tartaric acid and 152.3 g of oxalic acid dihydrate. The moist catalyst precursor was heated at 600° C. in the presence of air over a period of 10 hours.

Catalyst B

A solution of the active material was added to 1000 g of spherical alumina (Puralox® SCC a 80/120 from Condea-Chemie) as described in the case of catalyst A. The moist catalyst precursor was heated at 600° C. in the presence of air over a period of 10 hours.

According to sieve analysis, the two particle fractions A and B differ in the mean diameter by 45% relative to one another.

Examples 1 and 2 and Comparative Examples A and B

Ammoxidation of o-xylene

In a fluidized-bed reactor having a diameter of 6 cm and a height of 120 cm, a gas stream consisting of 3% by volume of o-xylene (ie. 120 g/h), 12% by volume of oxygen and 85% by volume of ammonia was passed at 470° C. over 600 g of catalyst. Four different catalysts were used.

Example 1

Mixture of 550 g of catalyst A+50 g of catalyst B

Example 2

Mixture of 500 g of catalyst A+100 g of catalyst B

Comparative Example A

Pure fraction of 600 g of catalyst A

Comparative Example B

Pure fraction of 600 g of catalyst B

The results are listed in the Table below:

TABLE

|  | Comparative Example A | Comparative Example B | Example 1 | Example 2 |
|---|---|---|---|---|
| Amount of catalyst [g] | 600 | 600 | 600 | 600 |
| Catalyst A [% by wt.] | 100 | 0 | 95 | 90 |
| Catalyst B [% by wt.] | 0 | 100 | 5 | 10 |
| Temperature [° C.] | 470 | 470 | 470 | 470 |
| Amount of o-xylene [g/h] | 120 | 120 | 120 | 120 |
| Conversion of o-xylene [%] | 93.5 | 93.7 | 94.5 | 94 |
| Phthalodinitrile yield [mol %] | 61.5 | 61.7 | 64.2 | 64.1 |
| g of phthalodinitrile/ h/100 g of catalyst | 89.1 | 89.4 | 93 | 92.9 |

We claim:

1. A process for the preparation of aromatic or heteroaromatic nitriles of the formula I

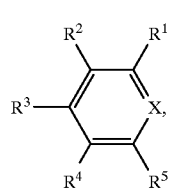

(I)

where
  X is nitrogen or C-$R^6$ and
  $R^1$, $R^2$, $R^3$, $R^4$, $R^5$ and $R^6$ are each hydrogen, $C_1$–$C_8$-alkyl, halogen, trifluoromethyl, nitro, amino, cyano, $C_1$–$C_7$-cyanoalkyl, $C_1$–$C_8$-aminoalkyl or hydroxyl, with the proviso that at least one of the substituents is cyano or $C_1$–$C_7$-cyanoalkyl, from aromatic or heteroaromatic hydrocarbons of the formula II

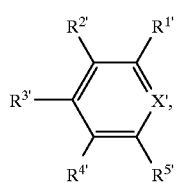

(II)

where
X' is nitrogen or C-R$^{6'}$ and
R$^{1'}$, R$^{2'}$, R$^{3'}$, R$^{4'}$, R$^{5'}$ and R$^{6'}$ are each hydrogen, C$_1$–C$_8$-alkyl, halogen, trifluoromethyl, nitro, amino, C$_1$–C$_8$-aminoalkyl or hydroxyl, with the proviso that at least one of the substituents is C$_1$–C$_8$-alkyl,
with ammonia and oxygen or oxygen-containing gases at from 200 to 600° C. and from 0.1 to 5 bar in the gas phase over supported catalysts which consists of from 0.5 to 20% by weight each of vanadium oxide and antimony oxide, wherein the supported catalysts consist of a mixture of from 2 to 4 different particle fractions whose mean diameters differ by from 10 to 80% and the carrier has a bulk density of from 0.6 to 1.2 kg/l.

2. A process as claimed in claim 1, wherein the reaction is carried out in a fluidized bed of said catalyst.

3. A supported catalyst comprising a mixture of from 2 to 30 different particle fractions whose mean diameters differ by from 10 to 80% and whose carrier has a bulk density of from 0.6 to 1.2 kg/l and which consists of from 0.5 to 20% by weight of vanadium oxide, from 0.5 to 20% by weight of antimony oxide, from 0 to 4% by weight of cesium oxide or rubidium oxide and from 0 to 10% by weight of one or more oxides selected from the group consisting of tungsten, molybdenum, titanium, iron, cobalt, nickel, manganese, potassium, copper or an alkaline earth metal, the carrier accounting for from 50 to 99.9% by weight of the total catalyst mass.

4. A supported catalyst as claimed in claim 3, wherein alumina, silica, titanium dioxide, zirconium dioxide or a mixture thereof is used as the carrier.

5. A process as claimed in claim 3, wherein the carrier is alumina.

6. A process as claimed in claim 1, wherein the carrier consists of alumina, silica, titanium dioxide, zirconium dioxide or a mixture thereof.

7. A process as claimed in claim 1, wherein the supported catalyst consists of from 1 to 10% by weight of vanadium oxide and from 1 to 10% by weight of antimony oxide.

8. A process as claimed in claim 1, wherein the supported catalyst consists of from 0.5 to 20% by weight of vanadium oxide and from 0.5 to 20% by weight of antimony oxide and from 0.01 to 4% by weight of cesium dioxide, rubidium oxide or a mixture thereof.

9. A supported catalyst as claimed in claim 3, wherein alumina, silica or a mixture thereof is used as the carrier.

10. A process for the preparation of the supported catalysts as claimed in claim 3, wherein a carrier having different mean particle diameters is impregnated simultaneously or in succession with a solution or suspension of from 0.5 to 20% by weight of vanadium oxide, from 1 to 20% by weight of antimony oxide, from 0 to 4% by weight of cesium oxide or rubidium oxide, from 0 to 10% by weight of one or more oxides selected from the group consisting of tungsten, molybdenum, titanium, iron, cobalt, nickel, manganese, copper, an alkali metal and an alkaline earth metal, the carrier accounting for from 50 to 99.9% by weight of the total catalytic mass, is dried and is calcined under oxidizing conditions at from 400 to 800° C.

11. A process for the preparation of the supported catalysts as claimed in claim 10, wherein vanadium in the form of the oxalate and antimony in the form of the tartrate are used.

* * * * *